United States Patent [19]
Boos et al.

[11] Patent Number: 5,403,917
[45] Date of Patent: Apr. 4, 1995

[54] PROCESS FOR THE QUANTITATIVE SELECTIVE REMOVAL OR PREPARATIVE ISOLATION OF TUMOUR NECROSIS FACTOR (TNF) OR/AND LIPOPOLYSACCHARIDES (LPS) FROM AQUEOUS LIQUIDS

[75] Inventors: Karl-Siegfried Boos, Gauting; Dietrich Siedel, Feldafing; Friedrich von der Haar, Melsungen, all of Germany

[73] Assignee: B. Braun Melsungen, AG, Melsungen, Germany

[21] Appl. No.: 132,316

[22] Filed: Oct. 6, 1993

[30] Foreign Application Priority Data

Oct. 12, 1992 [DE] Germany .................. 42 34 363.1
Sep. 15, 1993 [DE] Germany .................. 43 31 358.2

[51] Int. Cl.[6] .................. C07K 3/12; C07K 3/20; C07K 13/00; A61M 1/34
[52] U.S. Cl. .................. 530/351; 530/382; 530/412; 530/415; 530/416; 530/417; 604/5; 604/6; 436/86; 536/55.1; 536/123
[58] Field of Search .............. 424/85.1; 530/351, 382, 530/412, 415, 416, 417; 536/55.1, 123; 604/4, 5, 6; 436/86

[56] References Cited

U.S. PATENT DOCUMENTS

| | | |
|---|---|---|
| 3,959,128 | 5/1976 | Harris .................. 210/692 |
| 4,576,928 | 3/1986 | Tani .................. 502/404 |
| 4,777,242 | 10/1988 | Nelles .................. 530/351 |
| 4,880,915 | 11/1989 | Kajihara .................. 530/413 |
| 4,923,439 | 5/1990 | Seidel et al. .................. 604/6 |
| 4,935,204 | 6/1990 | Seidel et al. .................. 424/101 |
| 5,055,447 | 10/1991 | Palladino et al. .................. 514/12 |
| 5,059,654 | 10/1991 | Hou .................. 525/54.1 |
| 5,108,596 | 4/1992 | Ookuma et al. .................. 210/198.2 |
| 5,178,864 | 1/1993 | Lees et al. .................. 424/94.1 |
| 5,252,216 | 10/1993 | Folena Wasserman et al. ... 210/635 |

FOREIGN PATENT DOCUMENTS 9209520 10/1992 Rep. of Korea .

OTHER PUBLICATIONS

Ruff et. al. "Purification & Physico-Chemical Characterization of Rabbit Tumor Meciosis Factor" J. Immunol 125(4) 1671–1677, 1980.
Abbas et al "Cellular & Molecular Immunology" 229–232 1991.
The Merck Index Tenth Ed. "Polymyxin" & Polymyxin B–Methanesulfonic Acid p. 7448 (#'s 7445 & 7446).
Abstract of Korea Patent No. 9209520 issued Oct. 17, 1992 Bae et. al.
Derwent Abstract #93-293005/37.

Primary Examiner—Jeffrey E. Russel
Assistant Examiner—Nancy J. Gromet
Attorney, Agent, or Firm—Nikaido, Marmelstein, Murray & Oram

[57] ABSTRACT

For the quantitative selective removal or/and preparative isolation of tumour necrosis factor (TNF) or/and lipopolysaccharides from aqueous liquids, in particular blood, plasma or serum, the aqueous liquid is passed over an adsorption material which consists of a porous supporting material to which functional groups made of synthetic or/and semisynthetic or/and natural polyanion chains and namely in a linear or branched form, are covalently bound and if desired, the molecules chromatographically separated in this way are eluted from the adsorption material using a saline solution. A device according to the present invention for the extracorporeal removal of tumour necrosis factor and/or lipopolysaccharides (LPS) from aqueous liquids, in particular blood, plasma or serum, consists of a cylindrical housing which is filled with an adsorption material which consists of a porous supporting material to which functional groups made of synthetic or/and semisynthetic or/and natural polyanion chains and namely in a linear or branched form, are covalently bound and is provided with covers at its front ends which each have a central inlet and outlet.

24 Claims, 3 Drawing Sheets

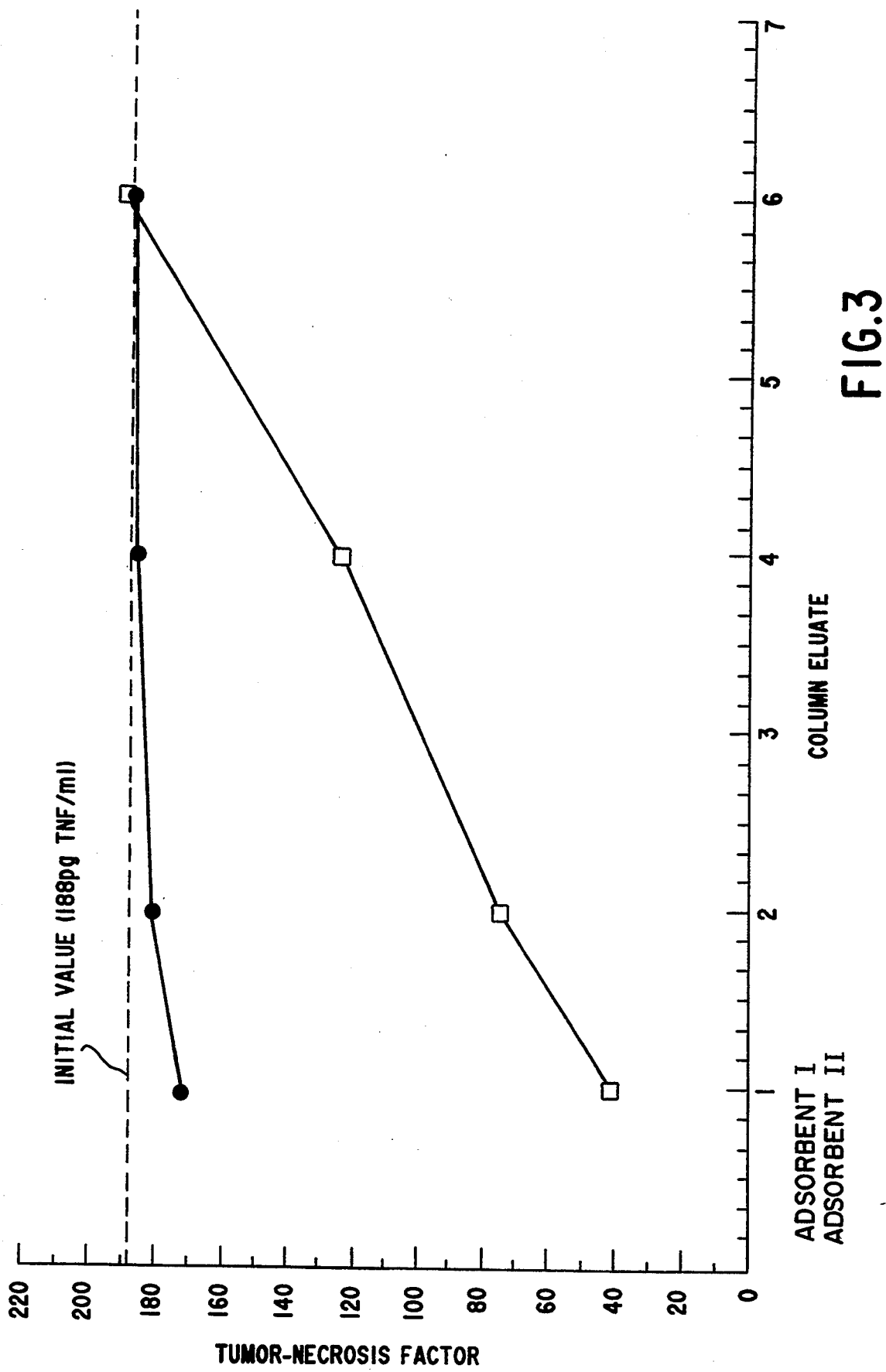

PROCESS FOR THE QUANTITATIVE SELECTIVE REMOVAL OR PREPARATIVE ISOLATION OF TUMOUR NECROSIS FACTOR (TNF) OR/AND LIPOPOLYSACCHARIDES (LPS) FROM AQUEOUS LIQUIDS

DESCRIPTION

The invention concerns a process for the removal or/and preparative isolation of tumour necrosis factor (TNF) and/or lipopolysaccharides (LPS) from aqueous liquids using porous supporting materials with covalently bound functional groups made of synthetic, semisynthetic and/or natural linear and/or branched polyanion chains as well as a device for carrying out the process.

In addition the invention concerns a method for the determination of the concentration of TNF in aqueous liquids.

The selective elimination of TNF and/or LPS from human blood and/or human plasma is desirable from a medical point of view in particular for the treatment of septic shock.

Septic shock arises as a complication when humans are infected by gram-negative bacteria. The prognosis for this clinical picture is poor with the current standard therapy. A fatal outcome is likely to occur in up to 50% of patients with septic shock despite all therapeutic measures. The number of deaths caused by septic shock in the USA is estimated as ca. 100000 per year (Parillo, J. E. "Septic Shock in Humans" in: Annals of Internal Medicine, Vol. 113, No. 3, 1990, 227–242). Thus a selective extracorporeal elimination of this pathogen is desirable from the point of view of intensive therapy also in particular because for example the administration of highly efficacious antibiotics or immunoglobulins or plasma replacement treatment does not substantially improve the prognosis.

The pathogenesis of septic shock begins with the invasion of gram-negative bacteria into the blood stream. When the bacteria disintegrate the infection leads to the release of lipopolysaccharides (LPS) from the outer bacterial membrane. These so-called endotoxins activate the macrophages and lead to the secretion of tumour necrosis factor (TNF). The LPS molecules have a rod-like form and are composed of three structurally different regions. Lipid A is responsible for the toxic properties. This subregion with a molecular weight of 2000 daltons consists of a phosphorylated D-glucosamine-disaccharide to which several long-chain fatty acids are bound like an ester or amide.

The tumour necrosis factor is a polypeptide (157 amino acids, molecular weight: $17 \times 10^3$ dalton) and, as a hormone of the immune system, is a member of the cytokine class. TNF plays a key role among these polypeptide mediators with regard to the pathogenesis of septic shock. Thus in patients with for example a menigococcic sepsis there is a correlation between the TNF concentration in plasma and the degree of septic shock symptoms or the later occurrence of death (Grau, G. E. et al., Immunol. Rec. 112, 1989, 49 ff.). Increased TNF plasma concentrations also occur in patients with parasitic diseases and other infections (Scuderi, P. et al., Lancet II, 1986, 1229 ff.). The clinical picture of sepsis also correlates in most cases with the time-course and level of the endotoxin concentration in blood (Nitsche, D. et al., Intensive Care Med. 12 Suppl., 1986, 185 ff.).

The object of the present invention is therefore to provide processes for the selective elimination of TNF and/or LPS from aqueous liquids, in particular from whole blood, plasma and/or serum which at the same time meet the requirements for a simple and safe application in an extracorporeal perfusion system for humans.

Understandably the utilization of these methods and the materials used for them also apply in vitro for analytical and/or preparative purposes.

The following prerequisites among others must be met in order to utilize such an isolation process ex vivo for medical and therapeutic purposes:

1) The elimination of the pathogen should be as selective as possible.
2) The elimination process should not activate any physiological protective mechanisms such as the complement system or coagulation system.
3) The binding capacity of the adsorbent should fulfill optimal practical requirements.
4) It must be possible to sterilize the adsorbent with heat or gamma rays.
5) The adsorbent should only have a minimal release of particles in the micrometer range.
6) The adsorbent should allow an adequately high flow rate in the range up to 200 ml/min.

This object is achieved according to the present invention by a process for the quantitative selective removal and/or preparative isolation of tumour necrosis factor (TNF) and/or lipopolysaccharides from aqueous liquids, in particular from blood, plasma or serum, which is characterized in that the aqueous liquid is passed over an adsorption material which is composed of a porous supporting material to which functional groups made of synthetic or/and semisynthetic or/and natural polyanion chains that are in a linear or branched form are covalently bound and if desired, the molecules separated chromatographically in such a manner are eluted from the adsorption material using a saline solution.

Preferred natural polyanions in the process according to the present invention, which are bound to an appropriate supporting matrix using methods known to a person skilled in the art, are biological polycarboxylic acids and/or polysulfonic acids such as sulfated polysaccharides (heparin, dextran sulfate, chondroitin sulfate etc.). The synthetic or semisynthetic polyanions which are preferred according to the present invention and are bound covalently to an appropriate supporting matrix with the aid of methods known to a person skilled in the art are polymers or copolymers of the following monomers:

1) Vinyl type, such as acrylic acid, methacrylic acid, vinylsulfonic acid, maleic acid etc.
2) Acrylic acid and/or methacrylic acid derivatives of the formula $H_2C=CR_1-CO-R_2$, in which the substituent $R_1$ is hydrogen or a methyl group and $R_2$ is an amidically or esterically linked linear and/or branch chained aliphatic sulfonic acid, carboxylic acid and/or phosphoric acid group.
3) Styrene type, such as styrene sulfonic acid, anethol sulfonic acid, styrene phosphoric acid etc.
4) Peptide type, such as glutamic acid, aspartic acid etc.
5) Nucleic acid type, such as adenosine-3',5'-diphosphate guanosine-3',5'-diphosphate etc.

The supporting matrix used in the process according to the present invention can be composed of porous glass, porous silica gel and/or silica gel coated with organic polymers or copolymers, cross-linked carbohydrates such as microgranular or regenerated and/or derivatized cellulose, dextrans and agarose and/or organic polymers or copolymers.

Adsorbents that have the stated properties have already been described such as in EP 0 143 369 (synthetic polyanions immobilized on silica gel), EP 0 110 409 and EP 0 225 867 (porous and/or derivatized cellulose gels to which synthetic or natural polyanions are covalently bound), U.S. Pat. No. 4,103,685 (natural anions bound to agarose beads), EP application 83 112 042 (natural polyanions immobilized on organic copolymers), DE 39 26 539 (tentacle cation exchanger based on copolymers), EP 0 424 698 (polyacrylic acid immobilized on an organic copolymer) and DE 36 17 672 (natural and synthetic polyanions bound to silica gel).

It is preferable to manufacture and use the previously described adsorbents for the selective adsorption of low-density lipoproteins (LDL), very-low-density lipoproteins (vLDL) and/or fibrinogen.

However, it unexpectedly turned out that such adsorbents also bind tumour necrosis factor (example 1) and lipopolysaccharides (example 2).

However, the results achieved with such adsorption materials are unsatisfactory with regard to a selective elimination of TNF and/or LPS in an extracorporeal perfusion system for medical and therapeutic purposes since the binding capacity and/or selectivity of these materials does not meet the optimal practical requirements.

The reason for these undesired properties is that such adsorbents preferably have average pore diameters of for example 20 nm to 1250 nm (EP 0 143 369) or 1000 nm (DE 36 17 672) and/or molecular exclusion limits for globular proteins of $5 \times 10^4$ to $5 \times 10^6$ daltons (DE 39 26 539), larger than $5 \times 10^5$ daltons (EP 0 424 698) and $1 \times 10^6$ to $1 \times 10^8$ daltons (EP 0 110 409 and EP 0 225 867) in order to preferentially adsorb biological macromolecules with a high binding capacity to the inner pore surface such as for example LDL with a particle diameter of 20-30 nm and a molecular weight of 2.2 to $3.5 \times 10^6$ daltons and/or fibrinogen with a molecular weight of $3.4 \times 10^5$ daltons.

Therefore according to the present invention supporting matrices are preferably used for the selective and effective elimination of TNF and/or LPS from body fluids, such as whole blood, plasma and/or serum, whose average pore diameter is less than 30 nm and/or whose molecular exclusion limit for globular proteins is smaller than $10^6$ daltons, preferably less than $2 \times 10^4$ daltons. In addition preferred supporting materials according to the present invention are used whose immobilized polyanions have an average molecular weight of 600 to $10^6$ daltons, preferably $5 \times 10^3$ to $5 \times 10^5$ daltons. When adsorbents structured in this way are used according to the present invention no undesired reactions occur in which macromolecules such as LDL and/or fibrinogen compete for the polyanionic adsorption centres in the pore interiors (comparative example 3).

Thus TNF and/or LPS can be eliminated very selectively and with a high specific binding capacity from body fluids in an extracorporeal perfusion system in the desired manner.

In addition the process according to the present invention enables TNF and/or LPS to be obtained in an extremely pure form by eluting the bound molecules from the column according to known methods and namely preferably using increasing gradients of sodium chloride solutions. After elution from the adsorption material the concentration of tumour necrosis factor or LPS can be determined according to known methods. The fractions obtained can then easily be pooled in such a way that particularly pure TNF or/and LPS is obtained.

In a preferred embodiment of the present invention, when using adsorption materials with an average pore diameter larger than 30 nm, a plasma fractionation filter which is impermeable to fibrinogen and/or LDL is used to obtain plasma before the subsequent selective elimination of TNF or/and LPS in order to achieve a pre-purification of the plasma which has a positive effect on the subsequent purification and isolation procedure. These two plasma constituents could impair the effectivity of the process according to the present invention. The separated constitutents can be immediately re-administed to the patient.

The invention in addition concerns a device for the extracorporeal removal of tumour necrosis factor and/or lipopolysaccharides from aqueous liquids, in particular blood, plasma or serum, in which this device consists of a cylindrical housing which is filled with an adsorption material as used in the processes according to the present invention and is provided with covers at its front ends which each have a central inlet and outlet. This cylindrical housing preferably has a diameter of 3 to 20 cm, preferably of 5 to 10 cm and a length of 1 to 40 cm, preferably 5 to 20 cm. The preferred material for the housing is glass or plastic.

In a further preferred embodiment of the device according to the present invention sieves with a pore diameter of 10 to 300 μm, preferably 20 to 100 μm are integrated into the covers for the elimination of particles. The device according to the present invention can be sterilized in a packaging by means of gamma rays or heat and is thus particularly suitable for use in an extracorporeal perfusion system. However, it can also be used practically as a chromatography column in particular for the determination according to the present invention of the concentration of tumour necrosis factor and/or for the preparative purification and isolation of tumour necrosis factor according to the present invention.

In a particularly preferred embodiment of the present invention the housing of the device is integrated into a closed circulation in which the aqueous liquid is circulated by means of a pump. In this case a plasma fractionation filter which is impermeable to fibrinogen and/or LDL can be preferably present in the circulation or even in a feed pipe to the circulation. This achieves a pre-purification and separation of LDL and also albumin in particular when using plasma. A device is particularly preferred with two cylindrical housings (two adsorber capsules) which can be operated alternately via valves and perfused with the aqueous liquid to be treated in a closed circulation by means of a pump. The capsule which at the time is not being perfused and which is saturated with tumour necrosis factor and/or LPS is eluted with a regeneration solution which is preferably a sodium chloride solution of high molarity. Aqueous solutions of amino compounds such as those described in EP 0 333 474 A2 are also suitable for the elution of LPS. In this case the membrane filter of course only needs to be present once if at all and preferably in a supply pipe for the aqueous liquid. Furthermore the invention concerns an adsorption material consisting of a porous supporting material with functional groups made of synthetic or/and semisynthetic or/and natural polyanion chains in a linear or branched form bound covalently thereto in which the average pore diameter of the supporting material is less than 30 nm and the molecular exclusion limit for globular proteins is less than $2 \times 10^4$ daltons. This adsorption material is quite especially suitable for carrying out the process according to the present invention.

BRIEF DESCRIPTION OF THE DRAWINGS

FIGS. 2 and 3 show that only absorbent I according to the present invention efficiently binds tumor necrosis factor in the desired manner and only small amounts of low density lipoproteins are absorbed whereas adsorbent II eliminates almost exclusively only the low density lipoproteins (LDL cholesterol).

The following examples are intended to elucidate the present invention in more detail in conjunction with the figures.

EXAMPLE 1

Elimination of TNF from human plasma

Adsorbent: dextran sulfate cellulose (Liposorber TM LA15, Kanegafuchi Chemical Industry, Osaka, Japan)

Experimental Procedure

Tumour necrosis factor (TNFα, Hofmann La-Roche, Basel) was added to 600 ml freshly obtained human plasma so that the concentration of TNF is 1410 pg/ml.

Subsequently the human plasma was pumped with a peristaltic pump at a flow rate of 10 ml/min over the adsorber capsule whose bed volume was ca. 150 ml and which had been equilibrated with a solution (Ringer's solution) consisting of NaCl (140 mmol/l), CaCl$_2$ (2 mmol/l) and KCl (4 mmol/l), pH 6.6.

The first 50 ml of the capsule eluate were discarded (dilution effects by means of capsule dead volume). The determination of TNF was carried out in the remaining eluate fractions each of 50 ml.

Figure 1:
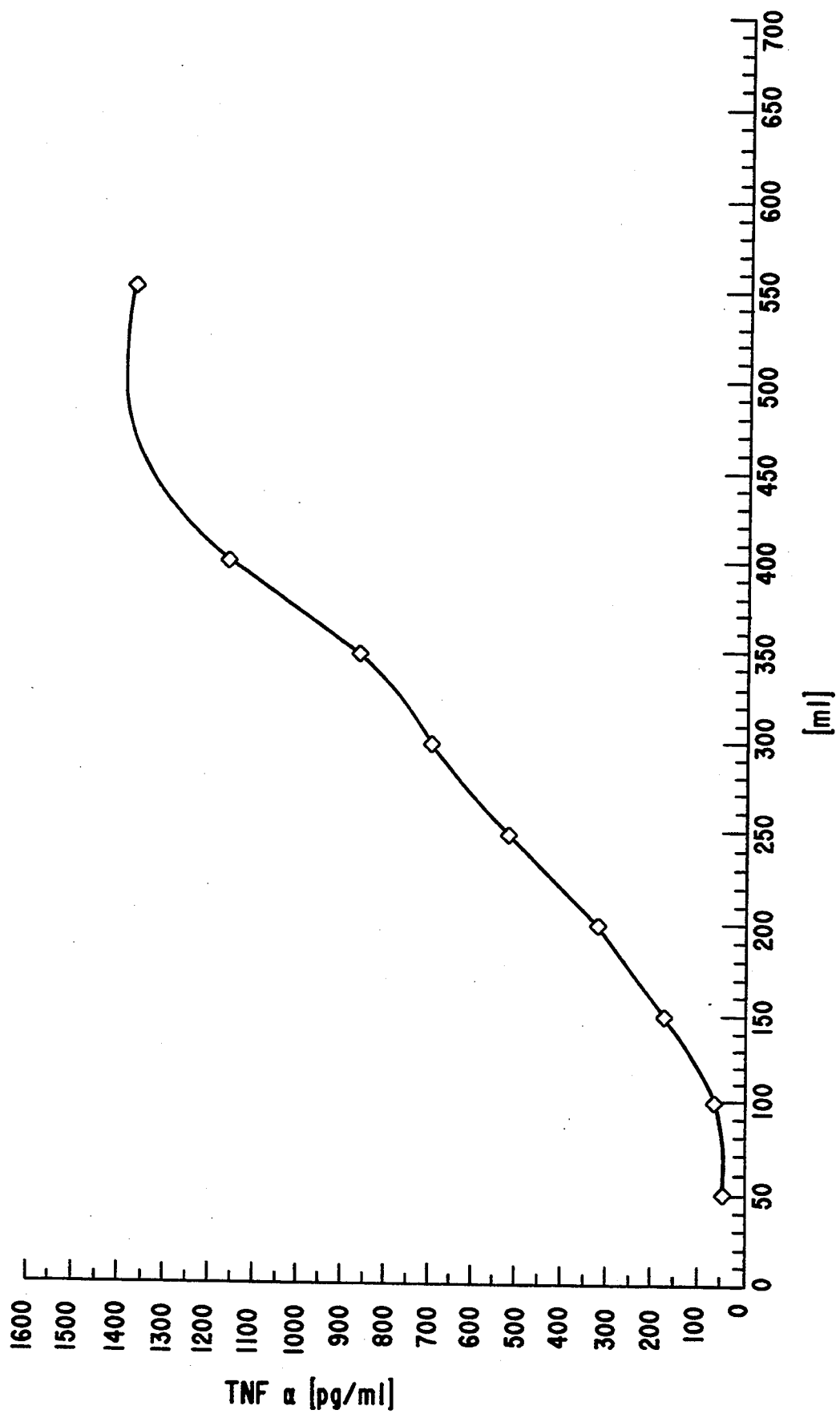
FIG. 1 shows that the dextran sulfate cellulose used according to the present invention completely eliminates tumor necrosis factor from the treated human plasma.

The shape of the adsorption curve in FIG. 1 shows that the dextran sulfate cellulose used according to the present invention completely eliminates tumour necrosis factor from the treated human plasma.

EXAMPLE 2

Elimination of Lipopolysaccharides (LPS) From Human Plasma

Adsorbent: dextran sulfate cellulose (Liposorber TM LA-15, Kanegafuchi Chemical Industry, Osaka, Japan).

Experimental Procedure 1200 pg E. coli endotoxin serotye 0111:B4 (LPS) was added to 10 ml freshly obtained human plasma. A disposable column (5×70 mm) was packed with dextran sulfate cellulose (column bed volume: 3 ml), equilibrated with Ringer's solution and sterilized by heat (121° C., 30 min). The LPS plasma was applied to the column under sterile conditions and the amount of LPS was determined in the eluate using the quantitative Limulus-Abmebocytelysate test (QCL-1000, Whittaker Co., Walkersville, Md.).

Experimental Result

The quantitative endotoxin test yielded a value of 850 pg LPS in the column eluate. Ca. 30% of the added amount of LPS was thus adsorbed or eliminated by the dextran sulfate cellulose used according to the present invention.

EXAMPLE 3

Comparative Investigation of Binding Capacity and Binding Selectivity For Tumour Necrosis Factor (TNF) From Human Serum Adsorbents I) Fractogel TSK HW 40 C (supplier: E. Merck, Darmstadt) with a fractionation range for globular proteins of $10^2$ to $10^4$ daltons, a particle size of 50 to 100 μm and an average pore diameter of 12 nm was activated with epichlorohydrin (1-chloro-2,3-epoxypropane) in a known manner and subsequently reacted with dextran sulfate (molecular weight: $5 \times 10^3$ daltons).

II) Fractogel TSK HW 65 M (supplier: E. Merck, Darmstadt) with a fractionation range for globular proteins of $5 \times 10^4$ to $5 \times 10^6$ daltons, a particle size of 45 to 90 μm and an average pore diameter of 100 nm was activated with epichlorohydrin (1-chloro-2,3-epoxypropane) in a known manner and subsequently reacted with dextran sulfate (molecular weight: $5 \times 10^3$ daltons).

Experimental Procedure

Tumour necrosis factor (TNF, Hofmann La-Roche, Basel) was added to 6 ml freshly obtained human serum so that the TNF concentration was 188 pg/ml. Subsequently this human serum sample was applied at room temperature to a column (5×80 mm; column bed volume: 2 ml) filled with adsorbent I or II and equilibrated with a solution (Ringer's solution, pH 6.6) consisting of NaCl (140 mmol/l), CaCl$_2$ (2 mmol/l) and KCl (4 mmol/l) and the concentration of tumour necrosis factor (TNF) and low-density lipoprotein cholesterol (LDL cholesterol) was determined in the column eluate (1 ml fractions). The results of the TNF and LDL cholesterol determination were applied depending on the eluate volume (FIG. 2 and FIG. 3).

Figure 2:
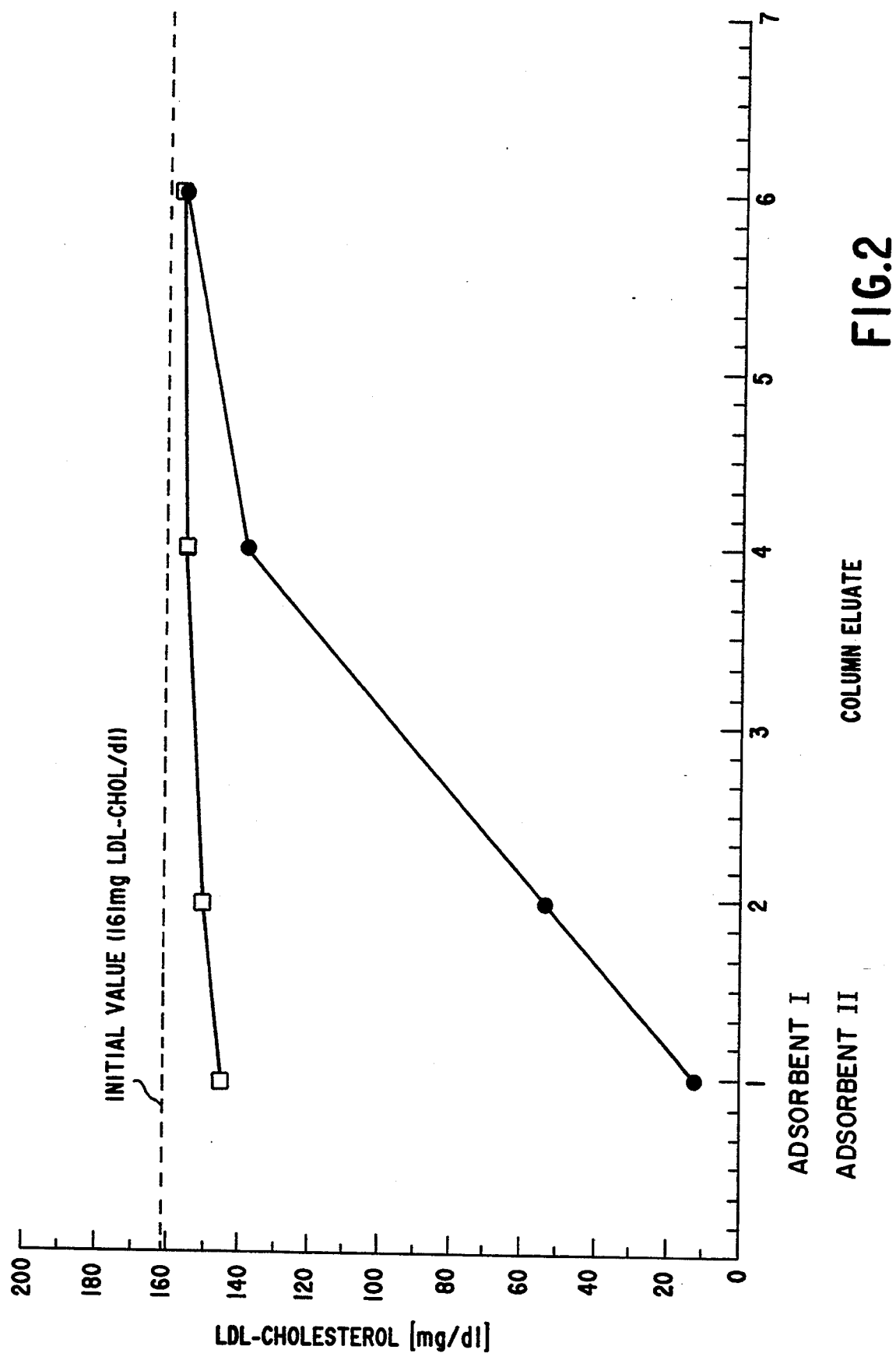

In FIG. 2 and FIG. 3 the shapes of the adsorption curves for TNF and LDL cholesterol show that only adsorbent I according to the present invention very efficiently binds tumour necrosis factor in the desired manner and only small amounts of low-density lipoproteins (LDL cholesterol) are adsorbed whereas adsorbent II eliminates almost exclusively only the low-density lipoproteins (LDL cholesterol).

We claim:

1. A process for the selective removal of tumor necrosis factor (TNF) and/or lipopolysaccharides (LPS) from a patient's body fluids by extracorporeal perfusion, comprising the steps of:
    a) passing a body fluid over an adsorption material, and
    b) then returning said body fluid to said patient,
    wherein said adsorption material comprises a porous supporting material covalently bound to linear or branched functional groups selected from the group consisting of biological polycarboxylic acids and polysulfonic acids.

2. The process according to claim 1, wherein said body fluid is selected from the group consisting of blood, plasma and serum.

3. The process according to claim 1, wherein said porous supporting material has an average pore diameter less than 30 nm.

4. The process according to claim 1, wherein said porous supporting material has a molecular exclusion limit for globular proteins of less than $10^6$ daltons.

5. The process according to claim 4, wherein said molecular exclusion limit is less than $2 \times 10^4$ daltons.

6. A process for the isolation of tumor necrosis factor (TNF) and/or lipopolysaccharides (LPS) from a patient's body fluids by extracorporeal perfusion, comprising the steps of:
 a) passing a body fluid over an adsorption material,
 b) then returning said body fluid to said patient, and
 c) eluting any TNF and/or LPS from said adsorption material using a 0.5 to 2.0 molar sodium chloride solution,
 wherein said adsorption material comprises a porous supporting material covalently bound to linear or branched functional groups selected from the group consisting of synthetic polyanion chains, semisynthetic polyanion chains and natural polyanion chains.

7. A process for the selective removal of tumor necrosis factor (TNF) and/or lipopolysaccharides (LPS) from a patient's body fluids by extracorporeal perfusion, comprising the steps of:
 a) passing a body fluid through a plasma fractionation filter, wherein said plasma fractionation filter is impermeable to fibrinogen and LDL,
 b) then passing said body fluid over an adsorption material, and
 c) then returning said body fluid to said patient,
 wherein said adsorption material comprises a porous supporting material covalently bound to linear or branched functional groups selected from the group consisting of synthetic polyanion chains, semisynthetic polyanion chains and natural polyanion chains.

8. The process according to claim 7, wherein said porous supporting material has an average pore diameter of at least 30 nm.

9. The process according to claim 7, wherein said synthetic polyanion chains, semisynthetic polyanion chains and natural polyanion chains have an average molecular weight of 600 to $10^6$ daltons.

10. The process according to claim 9, wherein said average molecular weight is between $5 \times 10^3$ to $5 \times 10^5$ daltons.

11. The process according to claim 7, wherein said natural polyanion chains are sulfated polysaccharides.

12. The process according to claim 7, wherein said synthetic polyanion chains and said semisynthetic polyanion chains are selected from the group consisting of a) polymers and copolymers of acrylic acid, methacrylic acid, vinyl sulfonic acid, and maleic acid, b) acrylic acid derivatives and methacrylic derivatives having the formula $H_2C=CR_1—CO—R_2$, in which the substituent $R_1$ is hydrogen or a methyl group and $R_2$ is an amidically or esterically linked linear or branch-chained aliphatic sulfonic acid, carboxylic acid or phosphoric acid group, c) styrene sulfonic acid, d) anethole sulfonic acid, e) styrene phosphoric acid, f) glutamic acid, g) aspartic acid, h) adenosine-3',5'-diphosphate, and i) guanosine-3',5'-diphosphate.

13. The process according to claim 7, wherein said porous supporting material is selected from the group consisting of porous glass, porous silica gel, silica gel coated with organic polymers or copolymers, cross-linked carbohydrates, organic polymers and organic copolymers.

14. The process according to claim 13, wherein said porous supporting material is cellulose and said functional group is dextran sulfate.

15. A method for the determination of the concentration of tumor necrosis factor in a body fluid, comprising the steps of:
 a) passing a body fluid over an adsorption material,
 b) eluting any TNF from said adsorption material using a 0.5 to 2.0 molar sodium chloride solution, and
 c) determining the concentration of any tumor necrosis factor eluted from said adsorption material as an indication of the concentration of tumor necrosis factor in said body fluid,
 wherein said adsorption material comprises a porous supporting material covalently bound to linear or branched functional groups selected from the group consisting of synthetic polyanion chains, semisynthetic polyanion chains and natural polyanion chains.

16. Device for the extracorporeal removal of tumor necrosis factor (TNF) and lipopolysaccharides (LPS) from body fluids, comprising a plasma fractionation filter which is impermeable to fibrinogen and LDL; in combination with a cylindrical housing with covers at both ends, wherein said covers have a central inlet and outlet and wherein said cylindrical housing is filled with an adsorption material comprising a porous supporting material covalently bound to linear or branched functional groups selected from the group consisting of synthetic polyanion chains, semisynthetic polyanion chains and natural polyanion chains.

17. Device according to claim 16, wherein said cylindrical housing has a diameter of 3 to 20 cm and a length of 1 to 40 cm.

18. Device according to claim 17, wherein said cylindrical housing has a diameter of 5 to 10 cm and a length of 5 to 20 cm.

19. Device according to claim 16, wherein said cylindrical housing is composed of glass or plastic.

20. Device according to claim 16, further comprising sieves in the covers to eliminate particles, wherein said sieves have a pore size of 10 to 200 μm.

21. Device according to claim 20, wherein said sieves have a pore size of 20 to 100 μm.

22. Device according to claim 16, wherein said cylindrical housing is part of a closed circuit in which said body fluid is circulated by means of a pump.

23. A method for the extracorporeal removal of tumor necrosis factor and lipopolysaccharides from body fluids, comprising:
 a) passing a body fluid through a device unit comprising two cylindrical housings, each with covers at both ends, wherein said covers have a central inlet and outlet and wherein said cylindrical housings are filled with an adsorption material comprising a porous supporting material covalently bound to linear or branched functional groups selected from the group consisting of biological polycarboxylic acids and polysulfonic acids,
 b) alternately perfusing the two cylindrical housings of the device unit with the body fluid to be treated, and
 c) rinsing the cylindrical housing which is not being perfused and which is saturated with tumor necrosis factor (TNF) and/or lipopolysaccharides (LPS) with a regeneration solution to elute bound tumor necrosis factor (TNF) and/or lipopolysaccharides (LPS).

24. The method according to claim 23, wherein said regeneration solution is a 0.5 to 2.0 molar sodium chloride solution.

* * * * *